United States Patent [19]

Smith

[11] 4,171,374

[45] Oct. 16, 1979

[54] ALKANOLAMINE DERIVATIVES

[75] Inventor: Leslie H. Smith, Macclesfield, England

[73] Assignee: Imperial Chemical Industries Limited, London, England

[21] Appl. No.: 878,446

[22] Filed: Feb. 16, 1978

Related U.S. Application Data

[62] Division of Ser. No. 738,173, Nov. 2, 1976, Pat. No. 4,083,992, which is a division of Ser. No. 607,995, Aug. 26, 1975, Pat. No. 4,010,189, which is a division of Ser. No. 421,669, Dec. 4, 1973, Pat. No. 3,928,412.

[30] Foreign Application Priority Data

Dec. 15, 1972 [GB] United Kingdom ............... 57970/72
Sep. 17, 1973 [GB] United Kingdom ............... 43478/73

[51] Int. Cl.$^2$ .................. A61K 31/17; A61K 31/215; A61K 31/275; C07C 127/19
[52] U.S. Cl. ............................. 424/304; 260/465 D; 260/553 A; 560/9; 560/22; 560/34; 562/426; 562/434; 562/439; 424/309; 424/319; 424/322
[58] Field of Search .......... 260/553 A, 553 R, 465 D; 424/304, 322, 309; 560/34; 562/439

[56] References Cited

U.S. PATENT DOCUMENTS

| | | | |
|---|---|---|---|
| 3,663,607 | 5/1972 | Barrett et al. .................... | 260/465 X |
| 3,712,927 | 1/1973 | Howe et al. ...................... | 260/465 X |
| 3,732,277 | 5/1973 | Koppe et al. .................... | 260/465 X |
| 3,928,412 | 12/1975 | Smith ............................... | 260/465 D |

*Primary Examiner*—Dolph H. Torrence
*Attorney, Agent, or Firm*—Cushman, Darby & Cushman

[57] ABSTRACT

Novel 1-aryloxy-3-amidoalkylamino-2-propanol derivatives, processes for their manufacture, pharmaceutical compositions containing them and methods of using them in the treatment of heart diseases. The compounds possess β-adrenergic blocking activity and some of them additionally possess cardiac stimulant activity. Representative of the compounds disclosed is 1-(2-fluorophenoxy)-3-β-(3-benzylureido) ethylamino-2-propanol.

15 Claims, No Drawings

ALKANOLAMINE DERIVATIVES

This application is a divisional continuation-in-part of application Ser. No. 738,173, filed Nov. 2, 1976 now U.S. Pat. No. 4,083,992, which is a divisional of application Ser. No. 607,995, filed Aug. 26, 1975 now U.S. Pat. No. 4,010,189, which itself is a divisional of application Ser. No. 421,669, filed Dec. 4, 1973 now U.S. Pat. No. 3,928,412.

This invention relates to new alkanolamine derivatives which possess β-adrenergic blocking activity.

According to the invention there is provided a new alkanolamine derivative of the formula:

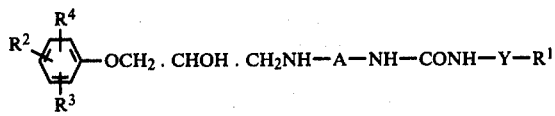

wherein A stands for an alkylene radical of from 2 to 12 carbon atoms; wherein $R^1$ stands for the hydrogen atom or for an alkyl, halogenoalkyl, alkenyl or cycloalkyl radical each of up to 10 carbon atoms, or for any aryl radical of the formula:

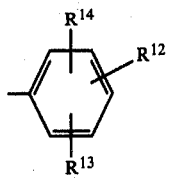

wherein $R^2$, $R^3$, $R^{12}$ and $R^{13}$, which may be the same or different, each stands for a hydrogen or halogen atom, a hydroxy, amino, nitro or cyano radical, an alkyl, cycloalkyl, alkenyl, alkynyl, alkoxy, alkylthio, cycloalkoxy, alkenyloxy, alkynyloxy or alkanoyl radical each of up to 6 carbon atoms, or an aryl, aryloxy or aralkoxy radical each of up to 12 carbon atoms; or wherein $R^2$ and $R^3$ together, and/or $R^{12}$ and $R^{13}$ together, form the trimethylene, tetramethylene, 1-oxotetramethylene, propenylene, but-2-enylene or buta-1,3-dienylene radical such that together with the adjacent benzene ring they form respectively the indanyl, 5,6,7,8-tetrahydronaphthyl, 5-oxo-5,6,7,8-tetrahydronaphthyl, indenyl, 5,8-dihydronaphthyl or naphthyl radical; wherein $R^4$ stands for the hydrogen atom or for the hydroxy or hydroxymethyl radical or for an aralkoxy radical of up to 12 carbon atoms; wherein $R^{14}$ stands for the hydrogen atom or for the amino radical or for a dialkylamino radical of up to 12 carbon atoms; and wherein Y stands for an alkylene, alkyleneoxy or alkylenecarbonyloxy radical each of up to 6 carbon atoms; or an acid-addition salt thereof.

It will be observed that the alkanolamine derivative of the invention possesses an asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for the alkylene radical A is, for example, the ethylene, trimethylene, tetramethylene, hexamethylene, dodecamethylene, 1-methylethylene, 2-methylethylene or 1,1-dimethylethylene radical. A is preferably the ethylene, 1-methylethylene or 1,1-dimethylethylene radical.

A suitable value for $R^1$ when it stands for an alkyl, halogenoalkyl, alkenyl or cycloalkyl radical is, for example, and methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, cycloalkyl, alkenyl, alkynyl, alkoxy, alkylthio, cycloalkoxy, alkenyloxy, alkynyloxy or alkanoyl radical is, for example, the methyl, ethyl, n-propyl, cyclopropyl, cyclopentyl, allyl, ethynyl, methoxy, isopropoxy, methylthio, cyclopentyloxy, allyloxy, propargyloxy, formyl or acetyl radical.

A suitable value for $R^2$, $R^3$, $R^{12}$ or $R^{13}$ when it stands for an aryl or aryloxy radical is, for example, the phenyl or phenoxy radical.

A suitable value for $R^2$, $R^3$, $R^4$, $R^{12}$ or $R^{13}$ when it stands for an aralkoxy radical is, for example, the benzyloxy radical.

A suitable value for $R^{14}$ when it stands for a dialkylamino radical is, for example, the dimethylamino radical.

A suitable value for Y is, for example, the methylene, ethylidene (—CH(CH$_3$)—), methyleneoxy, ethyleneoxy, 2,2-dimethylethyleneoxy or methylenecarbonyloxy radical.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

A preferred alkanolamine derivative of the invention is a compound of the formula given above wherein A stands for the ethylene, 1-methylethylene or 1,1-dimethylethylene radical, especially the ethylene radical, and wherein either:

(a) $R^1$ stands for the hydrogen atom or for an alkyl, radical of up to 6 carbon atoms, Y stands for an alkyleneoxy or alkylenecarbonyloxy radical each of up to 4 carbon atoms, $R^2$ stands for the hydrogen atom or for a fluoro, chloro, cyano or methyl radical, especially in the 2-position of the benezene nucleus, and $R^3$ and $R^4$ both stand for hydrogen atoms; or (b) $R^1$ stands for the unsubstituted phenyl radical, Y stands for an alkylene radical of 1 or 2 carbon atoms, especially methylene, and $R^2$, $R^3$ and $R^4$ have the meanings stated in paragraph (a) above; or (c) $R^1$ and Y have the meanings stated in paragraph (a) above, or $R^1$ and Y have the meanings stated in paragraph (b) above, $R^4$ stands for the hydroxy radical, especially in the 4-position of the benzene nucleus, and R² and R³ both stand for hydrogen atoms; or an acid-addition salt thereof.

Specific alkanolamine derivatives of the invention are those hereinafter described in the Examples. Of these, preferred compounds by virtue of their high cardioselective β-adrenergic blocking activity (as hereinafter defined) are:

1-(2-cyanophenoxy)-3-β-(3-benzylureido)ethylamino-2-propanol;
1-phenoxy-3-β-(3-β-hydroxyethylureido)ethylamino-2-propanol;
1-(2-fluorophenoxy)-3-β-(3-benzylureido)ethylamino-2-propanol; and
1-(2-cyanophenoxy)-3-β-(3-methoxymethylureido)ethylamino-2-propanol;

and the acid-addition salts thereof.

Preferred compounds by virtue of their high level of cardiac stimulant activity (as hereinafter defined) are:

1-(4-hydroxyphenoxy)-3-β-(3-methoxymethylureido)ethylamino-2-propanol; and
1-(4-hydroxyphenoxy)-3-β-(3-n-butyloxycarbonylmethylureido) ethylamino-2-propanol;

and the acid-addition salts thereof.

The alkanolamine derivative of the invention may be manufactured by any chemical process known to be useful for the manufacture of chemically-analogous compounds, particularly those processes disclosed in U.S. Pat. No. 3,928,412.

One preferred process for the manufacture of an alkanolamine derivative of the invention comprises the reaction of a compound of the formula

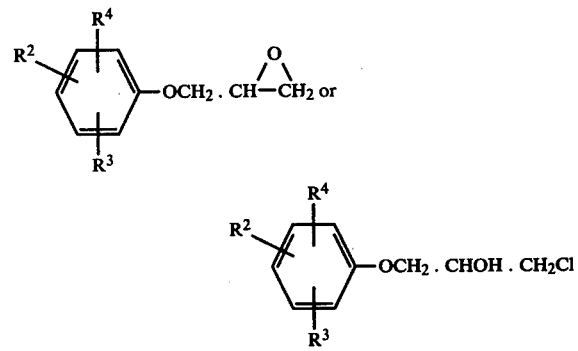

wherein R², R³ and R⁴ have the meanings stated above, with a compound of the formula

R⁶NH—A—NHCONH—Y—R¹ wherein A, R¹ and Y have the meanings stated above and wherein R⁶ stands for hydrogen or for a benzyl radical, whereafter if R⁶ stands for a benzyl radical this is removed by hydrogenolysis.

This process may be carried out in a diluent or solvent, for example ethanol, at a temperature of up to the boiling point of the diluent or solvent.

A second preferred process for the manufacture of an alkanolamine derivative of the invention comprises the reaction of a compound of the formula:

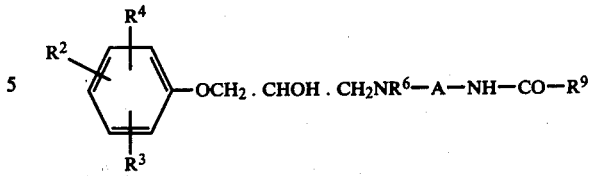

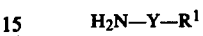

wherein A, R², R³, R⁴ and R⁶ have the meanings stated above and wherein R⁹ stands for a displaceable radical, for example the phenoxy radical, with an amine of the formula

H₂N—Y—R¹ wherein R¹ and Y have the meanings stated above, whereafter if R⁶ stands for a benzyl radical this is removed by hydrogenolysis.

This process may be carried out in a diluent or solvent, for example dioxan or toluene, and it may be carried out at a temperature of up to the boiling point of the diluent or solvent.

A compound wherein one or more of R², R³, R⁴, R¹² and R¹³ stands for an aryloxy radical, for example the benzyloxy radical, may be converted into the corresponding compound wherein one or more of R², R³, R⁴, R¹² and R¹³ stands for the hydroxy radical by hydrogenolysis.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O, O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardioselective. This activity may be determined by the reversal of isoprenaline-induced tachycardia in rats or cats, a standard test for the determination of β-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathominetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is up to ten times more active as a cardioselective $\beta$-adrenergic blocking agent than practolol. At doses of an alkanolamine derivative of the invention which produce effective $\beta$-adrenergic blockade in rats or cats, no symptoms of toxicity are apparent.

Some of the alkanolamine derivatives of the invention wherein one or more of the substituents $R^2$, $R^3$ and $R^4$ stands for the hydroxy radical, and in particular those wherein $R^4$ stands for a hydroxy radical in the 3- or 4-position of the benzene nucleus, $R^2$ stands for the hydrogen atom or for a hydroxy radical in the 3-position when $R^4$ is in the 4-position of the benzene nucleus and $R^3$ stands for the hydrogen atom possess, in addition to $\beta$-adrenergic blocking activity, substantial cardiac stimulant activity. The stimulant activity may be demonstrated in either conscious or pentobarbitone-anaesthetised dogs, where the alkanolamine derivative or salt thereof produces an increase in heart rate, and/or an increase in force of contraction of the heart and an increase in the speed of conduction of electrical activity through the tissues of the heart. Unlike isoprenaline, a known cardiac stimulating agent, a preferred stimulant alkanolamine derivative of the invention or a salt thereof is well absorbed when administered orally and has a substantial duration of action. At doses of an alkanolamine derivative of the invention which produce effective cardiac stimulation in dogs, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; $\alpha$-adrenergic blocking agents, for example phentolamine and sympathomimetic bronchodilators, for example isoprenaline, orciprenaline, adrenaline and epherdrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

When used for the treatment of acute or chronic heart failure in man, it is expected that a cardiac stimulant alkanolamine derivative would be given to man at a total oral dose of between 10 mg. and 200 mg. daily, at doses spaced at 6–8 hourly intervals, or at an intravenous dose of between 1 mg. and 100 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

Methoxymethyl isocyanate is added slowly to a solution of 8.12 g. of 1-benzyloxphenoxy-3-(N-benzyl-N-$\beta$-aminoethyl)amino-2-propanol in 50 ml. of toluene which is maintained at laboratory temperature. The mixture is diluted with petroleum ether and filtered and the solid residue is crystallised from a mixture of ethyl acetate and petroleum ether. There is thus obtained 1-p-benzyloxyphenoxy-3-[N-benzyl-N-$\beta$-(3-methoxymethylureido)ethyl]amino-2-propanol.

A solution of 6.55 g. of the above product in acetic acid is shaken with hydrogen in the pressence of a 30% palladium-on-charcoal catalyst at laboratory temperature and atmospheric pressure until 500 ml. of hydrogen have been absorbed and the uptake of hydrogen ceases. The mixture is filtered, the filtrate is evaporated to dryness and the residue is converted into an oxalate salt which is hygroscopic, and for which no melting point is obtainable. There is thus obtained 1-p-hydroxyphenoxy-3-$\beta$-(3-methoxymethylureido)ethylamino-2-propanol oxalate.

The 1-p-benzyloxyphenoxy-3-(N-benzyl-N-$\beta$-aminoethyl) amino-2-propanol used as starting material may be obtained as follows:

A mixture of 51.2 g. of 1-p-benzyloxyphenoxy-2,3-epoxypropane, 51.3 g. of N-benzyl-N-$\beta$-isobutyramidoethylamine hydrochloride, 200 ml. of aqueous N-sodium hydroxide solution and 600 ml. of isopropanol is heated under reflux for 17 hours and then evaporated to dryness under reduced pressure. The residue is shaken with a mixture of chloroform and water and the chloroform layer is dried and evaporated to dryness.

The residue is added to a solution of 200 g. of potassium hydroxide in 400 ml. of ethanol and the mixture is heated under reflux for 96 hours and then diluted with water and extracted with ether. The ethereal extract is washed with water, dried and evaporated to dryness. There is thus obtained as oily residue 1-p-benzyloxyphenoxy-3-(N-benzyl-N-$\beta$-aminoethyl)amino-2-propanol which is used without further purification.

EXAMPLE 2

The process described in Example 1 is repeated except that n-butyloxycarbonylmethyl isocyanate is used in place of methoxymethyl isocyanate. There is thus obtained 1-p-hydroxyphenoxy-3-$\beta$-(3n-butyloxycarbonylmethylureido)ethylamino-2-propanol oxalate, which also is hygroscopic and for which no melting point is obtainable.

EXAMPLE 3

A solution of methoxymethyl isocyanate (0.43 g.) in acetonitrile (10 ml.) is added during 10 minutes to a solution of 1-o-cyanophenoxy-3-$\beta$-aminoethylamino-2-propanol (1.4 g.) in acetonitrile (50 ml.) which is kept at $-30°$ C., and the mixture is allowed to warm up to room temperature and is then filtered. The solid product is crystallised from acetonitrile and there is thus obtained 1-o-cyanophenoxy-3-$\beta$-(3-methoxymethylureido) ethylamino-2-propanol, m.p. 139°–141° C.

EXAMPLE 4

A stirred mixture of 1-(2-cyanophenoxy)-2,3-epoxypropane (1.75 g.), 1-($\beta$-aminoethyl)-3-benzylurea (1.93 g.), water (50 ml.) and ethanol (25 ml.) is heated at 90° C. for 16 hours and then evaporated to dryness under reduced pressure. Aqueous 2N-hydrochloric acid (100 ml.) is added, the mixture is washed twice with ethyl acetate (75 ml. each time) and the aqueous solution is then basified to pH 12 with concentrated aqueous sodium hydroxide solution. The mixture is extracted three times with ethyl acetate (100 ml. each time) and the combined extracts are washed with water, dried over magnesium sulphate and evaporated to dryness. The residue is crystallised from acetonitrile and there is thus obtained 1-(2-cyanophenoxy)-3-$\beta$-(3-benzylureidoethyl)amino-2-propanol, m.p. 147°–149° C.

The process described above is repeated except that the 1-(2-cyanophenoxy)-2,3-epoxypropane is replaced by the appropriate 1-phenoxy-2,3-expoxypropane. There are thus obtained the compounds shown in the following table:

R²–⟨phenyl⟩–OCH₂.CHOH.CH₂NHCH₂CH₂NHCONHCH₂–⟨phenyl⟩

| R² | m.p.(°C.) | crystallisation solvent |
| --- | --- | --- |
| 2-methyl | 156–157 | ethanol |
| 2-chloro | 162 | ethanol |
| 2-fluoro | 144–146 | methyl isobutyl ketone |
| 3-fluoro | 152 | aqueous isopropanol |
| 4-fluoro | 136–138 | methyl isobutyl ketone |
| 2-methoxy | 151–152 | ethanol |

The 1-($\beta$-aminoethyl)-3-benzylurea used as starting material may be obtained as follows:

Benzylamine (53.5 g.) is added during 30 minutes to a stirred suspension of phenyl chloroformate (78.3 g.) and anhydrous potassium carbonate (151.8 g.) in dioxan (500 ml.) and the mixture is stirred at laboratory temperature for 72 hours and then poured into water. The mixture is extracted with ethyl acetate and the extract is washed with water, dried over magnesium sulphate and evaporated to dryness. The residue is stirred with petroleum ether (b.p. 60°–80° C.) and the mixture is filtered. There is thus obtained as solid residue phenyl N-benzylcarbamate, which is used without further purification.

A mixture of phenyl N-benzylcarbamate (90.8 g.) and 1,2-diaminoethane (120 g.) is stirred at laboratory temperature for 16 hours and is then poured into water (500 ml.). The mixture is filtered and the filtrate is evaporated to dryness under reduced pressure. Toluene is added to the residue and removed by evaporation repeatedly until the residue crystallises. The residue is then recrystallised from a mixture of petroleum ether (b.p. 60°–80° C.) and toluene. There is thus obtained 1-($\beta$-aminoethyl)-3-benzylurea, m.p. 231° C.

EXAMPLE 5

A stirred mixture of phenyl N-$\beta$-(N-benzyl-N-3-p-benzyloxyphenoxy-2-hydroxypropyl)ethylcarbamate (5.26 g.), ethanolamine (1.2 g.) and toluene (50 ml.) is heated at 95°–100° C. for 16 hours and then cooled. Diethyl ether (200 ml.) is added, and sufficient n-butanol is then added to produce a homogeneous solution. The solution is extracted with aqueous N-sodium hydroxide solution (20 ml.) and three times with saturated aqueous sodium chloride solution (20 ml. each time). The organic solution is then dried over magnesium sulphate and evaporated to dryness, and the residue is dissolved in glacial acetic acid (80 ml.). A 30% palladium-on-charcoal catalyst (50 mg.) is added and the mixture is shaken with hydrogen at laboratory temperature and atmospheric pressure until 480 ml. of hydrogen have been absorbed. The mixture is filtered and the filtrate is evaporated to dryness under reduced pressure. The residue is dissolved in ethanol (10 ml.) and a solution of oxalic acid (0.63 g.) in ethanol (5 ml.) is added. The mixture is filtered and there is thus obtained as solid residue 1-p-hydroxyphenoxy-3-$\beta$-(3-$\beta$-hydroxyethylureido)ethylamino-2-propanol hydrogen oxalate, m.p. 145°–147° C.

The process described above is repeated except that either 2-amino-2-methylpropanol, $\beta$-methoxyethylamine or benzylamine is used in place of ethanolamine. There is thus obtained respectively 1-p-hydroxyphenoxy-3-$\beta$-[3-(2-hydroxy-1,1-dimethylethyl)ureido]ethylamino-2-propanol, which forms a hydroscopic hydrochloride after crystallisation from water; 1-p-hydroxyphenoxy-3-$\beta$-(3-$\beta$-methoxyethylureido)-ethylamino-2-propanol, characterised as its hydrogen oxalate, m.p. 126°–128° C. after crystallisation from ethanol; and 1-p-hydroxyphenoxy-3-$\beta$-(3-benzylureido)ethyl-amino-2-propanol, characterised as its hydrochloride, m.p. 113°–130° C. after crystallisation from ethanol.

The phenyl N-$\beta$-(N-benzyl-N-3-p-benzyloxyphenoxy-2-hydroxypropyl)ethyl carbamate used as starting material may be obtained as follows:

Phenyl chloroformate (17.22 g.) is added during 10 minutes to a stirred mixture of 1-p-benzyloxyphenoxy-3-(N-benzyl-N-$\beta$-aminoethyl)amino-2-propanol (40.6 g.), sodium bicarbonate (10.08 g.) and toluene (100 ml.) which is maintained at 0° C. After a further 5 minutes water is added and the mixture is extracted with ethyl acetate. The extract is washed with water, dried over magnesium sulphate and evaporated to dryness under reduced pressure. The residue is stirred with petroleum ether (b.p. 60°–80° C.) and then with toluene, and the mixture is filtered The solid product consists of phenyl N-$\beta$-(N-benzyl-N-3-p-benzyloxyphenoxy-2-hydroxypropyl)ethyl carbamate, which is used without further purification.

EXAMPLE 6

A stirred mixture of phenyl N-β-(N-benzyl-N-3-phenoxy-2-hydroxypropyl)ethylcarbamate [4.2 g.; prepared by similar means to those described in the last part of Example 5 from 1-phenoxy-3-(N-benzyl-N-β-aminoethyl)amino-2-propanol], benzylamine (1.18 g. and dioxan (20 ml.) is heated at 95°–100° C. for 18 hours and then cooled. Water is added and the mixture is extracted with ethyl acetate. The extract is dried over magnesium sulphate and evaporated to dryness, and the residue is redissolved in ethyl acetate. A solution of oxalic acid in ethyl acetate is added, and the mixture is filtered. The solid product is dissolved in glacial acetic acid and hydrogenated over a 30% palladium-on-charcoal catalyst by a similar method to that described in Example 5. The filtrate after removal of catalyst is evaporated to dryness and the residue is crystallised from a mixture of ethanol and ethyl acetate. There is thus obtained 1-phenoxy-3-β-(3-benzylureido)ethylamino-2-propanol hydrogen oxalate hemihydrate, m.p. 94°–96° C. (with decomposition).

The process described above is repeated except that either α-methylbenzylamine, ethanolamine or β-methoxyethylamine is used in place of benzylamine. There are thus obtained respectively 1-phenoxy-3-β-(3-α-methylbenzylureido)ethylamino-2-propanol, characterised as its hydrogen oxalate hemihydrate, m.p. 93°–95° C. after crystallisation from ethyl acetate; 1-phenoxy-3-β-(3-β-hydroxyethyl-ureido)ethylamino-2-propanol, characterised as its hydrogen oxalate monohydrate, m.p. 74° C. (with decomposition) after crystallisation from ethanol; and 1-phenoxy-3-β-(3-β-methoxyethylureido)ethylamino-2-propanol, characterised as its monohydrate, m.p. 85°–86° C., after crystallisation from ethyl acetate.

What we claim is:

1. An alkanolamine selected from compounds of the formula:

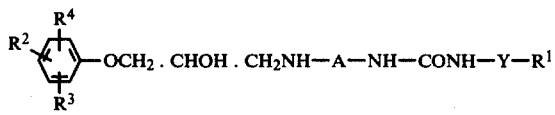

wherein A is alkylene of from 2 to 12 carbon atoms, wherein $R^1$ is hydrogen, or alkyl, halogenoalkyl, alkenyl or cycloalkyl each of up to 10 carbon atoms, or aryl of the formula:

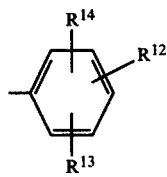

wherein $R^2$, $R^3$, $R^{12}$ and $R^{13}$, which may be the same or different, each is hydrogen, halogen, hydroxy, amino, nitro or cyano, alkyl, cycloalkyl, alkenyl, alkoxy, alkylthio, cycloalkoxy, alkenyloxy, alkynyloxy or alkanoyl each of up to 6 carbon atoms; or aryl, aryloxy or aralkoxy each of up to 12 carbon atoms; or wherein $R^2$ and $R^3$ together, and/or $R^{12}$ and $R^{13}$ together, are trimethylene, tetramethylene, 1-oxotetramethylene, propenylene, but-2-enylene or buta-1,3-dienylene such that together with the adjacent benzene ring they form respectively indanyl, 5,6,7,8-tetrahydronaphthyl, 5-oxo-5,6,7,8-tetrahydronaphthyl, indenyl, 5,8-dihydronaphthyl or naphthyl; wherein $R^4$ is hydrogen, hydroxy or hydroxymethyl or aralkoxy of up to 12 carbon atoms; wherein $R^{14}$ is hydrogen, amino or dialkylamino of up to 12 carbon atoms; and wherein when $R^1$ is hydrogen, alkyl, halogenoalkyl or alkenyl, Y is alkyleneoxy or alkylenecarbonyloxy each of up to 6 carbon atoms and when $R^1$ is cycloalkyl or aryl Y is alkylene, alkyleneoxy or alkylenecarbonyloxy each of up to 6 carbon atoms; and the acid-addition salts thereof.

2. An alkanolamine as claimed in claim 1 selected from compounds of the formula given in claim 1 wherein A is ethylene, trimethylene, tetramethylene, hexamethylene, dodecamethylene, 1-methylethylene, 2-methylethylene or 1,1-dimethylethylene; wherein $R^1$ is hydrogen, methyl, ethyl, n-propyl, isopropyl, n-butyl, isobutyl, t-butyl, n-pentyl, n-octyl, trifluoromethyl, allyl, cyclopropyl, cyclopentyl or cyclohexyl, or aryl of the formula:

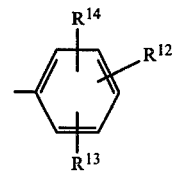

wherein $R^2$, $R^3$, $R^{12}$ and $R^{13}$, which may be the same or different, each is hydrogen, fluorine, chlorine, bromine, iodine, hydroxy, amino, nitro, cyano, methyl, ethyl, n-propyl, cyclopropyl, cyclopentyl, allyl, ethynyl, methoxy, isopropoxy, methylthio, cyclopentyloxy, allyloxy, propargyloxy, formyl, acetyl, phenyl, phenoxy or benzyloxy, or wherein $R^2$ and $R^3$ together and/or $R^{12}$ and $R^{13}$ together are trimethylene, tetramethylene, 1-oxotetramethylene, propenylene, but-2-enylene or buta-1,3-dienylene; wherein $R^4$ is hydrogen, hydroxy, hydroxymethyl or benzyloxy; wherein $R^{14}$ is hydrogen, amino or dimethylamino; and wherein when $R^1$ is hydrogen, methyl, ethyl, n-propyl, isopropyl, n-butyl, isobutyl, t-butyl, n-pentyl, n-octyl, trifluoromethyl or allyl, Y is methyleneoxy, ethyleneoxy, 2,2-dimethylethyleneoxy or ethylenecarbonyloxy; and when $R^1$ is cyclopropyl, cyclopentyl, cyclohexyl or aryl, Y is methylene, ethylidene, methyleneoxy, ethyleneoxy, 2,2-dimethyl ethyleneoxy or ethylenecarbonyloxy; and the acid-addition salts thereof.

3. An alkanolamine as claimed in claim 1 selected from compounds of the formula given in claim 1 wherein A is ethylene, 1-methylethylene or 1,1-dimethylethylene, $R^1$ is hydrogen or alkyl of up to 6 carbon atoms, Y is alkyleneoxy or alkylenecarbonyloxy each of up to 4 carbon atoms, $R^2$ is hydrogen, fluoro, chloro, cyano or methyl and $R^3$ and $R^4$ are both hydrogen; and the acid-addition salts thereof.

4. An alkanolamine as claimed in claim 3 wherein A is ethylene and $R^2$ is fluoro, chloro, cyano or methyl in the 2-position of the benzene nucleus.

5. An alkanolamine as claimed in claim 1 selected from compounds of the formula given in claim 1 wherein A is ethylene, 1-methylethylene or 1,1-dimethylethylene, $R^1$ is unsubstituted phenyl, Y is alkylene of 1 or 2 carbon atoms, $R^2$ is hydrogen, fluoro, chloro, cyano or methyl and $R^3$ and $R^4$ are both hydrogen; and the acid-addition salts thereof.

6. An alkanolamine as claimed in claim 5 wherein A is ethylene, Y is methylene and $R^2$ is fluoro, chloro, cyano or methyl in the 2-position of the benzene nucleus.

7. An alkanolamine as claimed in claim 1 selected from compounds of the formula given in claim 1 wherein A is ethylene, 1-methyethylene or 1,1-dimethylethylene, $R^1$ is hydrogen or alkyl of up to 6 carbon atoms and Y is alkyleneoxy or alkylenecarbonyloxy each of up to 4 carbon atoms, or $R^1$ is unsubstituted phenyl and Y is alkylene of 1 or 2 carbon atoms, $R^4$ is hydroxy and $R^2$ and $R^3$ are both hydrogen; and the acid-addition salts thereof.

8. An alkanolamine as claimed in claim 7 wherein A is ethylene and $R^4$ is hydroxy in the 4-position of the benzene nucleus.

9. An alkanolamine as claimed in claim 1 selected from:

1-(2-cyanophenoxy)-3-β-(3-benzylureido)ethylamino-2-propanol;

1-phenoxy-3-β-(3-β-hydroxymethylureido)ethylamino-2-propanol;

1-(2-fluorophenoxy)-3-β-(3-benzylureido)ethylamino-2-propanol; and 1-(2-cyanophenoxy)-3-β-(3-methoxymethylureido)ethylamino-2-propanol;

and the acid-addition salts thereof.

10. An alkanolamine as claimed in claim 1 selected from 1-(4-hydroxyphenoxy)-3-β-(3-methoxymethylureido)ethylamino-2-propanol; and 1-(4-hydroxyphenoxy)-3-β-(3-n-butyloxycarbonylmethylureido) ethylamino-2-propanol;

and the acid-addition salts thereof.

11. An acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-naphthoate), or a salt derived from a sulphonated polystyrene resin.

12. A pharmaceutical composition comprising as active ingredient at least one alkanolamine or an acid-addition salt thereof, claimed in claim 1, in association with a pharmaceutically-acceptable diluent or carrier therefor.

13. A method for the treatment or prophylaxis of heart diseases and hypertension in a warm-blooded animal which comprises administering to said animal an effective amount of at least one compound claimed in claim 1.

14. A method for producing coronary β-adrenergic blockage in a warm-blooded animal in need of such blockade which comprises administering to said animal an effective amount of at least one compound claimed in claim 1.

15. A method for the treatment of acute or chronic heart failure in a warm-blooded animal which comprises administering to said animal an effective amount of at least one cardiac stimulant alkanolamine, claimed in claim 1, which has the formula given in claim 1 wherein one or more of the substituents $R^2$, $R^3$ and $R^4$ is hydrogen and the other substituents are as defined in claim 1.

* * * * *